(12) United States Patent
Lindsay et al.

(10) Patent No.: US 12,031,981 B2
(45) Date of Patent: Jul. 9, 2024

(54) METHOD FOR ELECTRONIC DETECTION AND QUANTIFICATION OF ANTIBODIES

(71) Applicant: Arizona Board of Regents on behalf of Arizona State University, Scottsdale, AZ (US)

(72) Inventors: Stuart Lindsay, Scottsdale, AZ (US); Bintian Zhang, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 806 days.

(21) Appl. No.: 17/053,522

(22) PCT Filed: May 8, 2019

(86) PCT No.: PCT/US2019/031394
§ 371 (c)(1),
(2) Date: Nov. 6, 2020

(87) PCT Pub. No.: WO2019/217600
PCT Pub. Date: Nov. 14, 2019

(65) Prior Publication Data
US 2021/0231650 A1    Jul. 29, 2021

Related U.S. Application Data

(60) Provisional application No. 62/668,982, filed on May 9, 2018.

(51) Int. Cl.
*G01N 27/327* (2006.01)
*G01N 33/487* (2006.01)
(Continued)

(52) U.S. Cl.
CPC ... *G01N 33/5438* (2013.01); *G01N 33/48721* (2013.01); *G01N 33/6854* (2013.01); *G01N 2469/20* (2013.01)

(58) Field of Classification Search
CPC ......... G01N 33/48721; G01N 33/5438; G01N 33/6854; G01N 2469/20
See application file for complete search history.

(56) References Cited

U.S. PATENT DOCUMENTS

| 5,198,543 A | 3/1993 | Blanco |
| 6,824,974 B2 | 11/2004 | Pisharody et al. |

(Continued)

FOREIGN PATENT DOCUMENTS

| CN | 104359946 | 2/2015 |
| JP | 2016188794 A | 11/2016 |

(Continued)

OTHER PUBLICATIONS

Sela-Culang et al., "The structural basis of antibody-antigen recognition," frontiers in Immunology Oct. 2013|vol. 4|Article 302|1-13 (Year: 2013).*

(Continued)

*Primary Examiner* — Alexander S Noguerola
(74) *Attorney, Agent, or Firm* — Casimir Jones, S.C.; Peter J. Schlueter

(57) ABSTRACT

The present disclosure relates to a sensing device and methods for detecting, and quantifying the amount of, a target protein in a sample.

10 Claims, 8 Drawing Sheets

(51) Int. Cl.
*G01N 33/543* (2006.01)
*G01N 33/68* (2006.01)

(56) References Cited

U.S. PATENT DOCUMENTS

| | | |
|---|---|---|
| 7,632,671 B2 | 12/2009 | Tong |
| 8,628,649 B2 | 1/2014 | Lindsay et al. |
| 8,961,757 B2 | 2/2015 | Nuckolls et al. |
| 8,968,540 B2 | 3/2015 | Reinhart et al. |
| 9,140,682 B2 | 9/2015 | Lindsay et al. |
| 9,274,430 B2 | 3/2016 | Gyarfas et al. |
| 9,376,713 B2 | 6/2016 | Bashir et al. |
| 9,593,372 B2 | 3/2017 | Lindsay et al. |
| 9,938,586 B2 | 4/2018 | Liang et al. |
| 10,051,722 B2 | 12/2018 | Jin et al. |
| 10,227,694 B2 | 3/2019 | Jin et al. |
| 10,378,103 B2 | 8/2019 | Jin et al. |
| 10,379,102 B2 | 8/2019 | Lindsay et al. |
| 10,422,787 B2* | 9/2019 | Lindsay ............ G01N 27/44791 |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,648,941 B2 | 5/2020 | Merriman et al. |
| 10,712,334 B2 | 7/2020 | Choi et al. |
| 10,737,263 B2 | 8/2020 | Choi et al. |
| 10,913,966 B2 | 2/2021 | Merriman et al. |
| 2003/0124572 A1 | 7/2003 | Umek et al. |
| 2004/0146863 A1 | 7/2004 | Pisharody et al. |
| 2004/0249124 A1 | 12/2004 | Caruso et al. |
| 2005/0285275 A1 | 12/2005 | Son et al. |
| 2009/0215156 A1 | 8/2009 | Chung et al. |
| 2009/0226899 A1 | 9/2009 | Chen |
| 2010/0084276 A1 | 4/2010 | Lindsay |
| 2010/0184062 A1 | 7/2010 | Steinmuller-Nethl et al. |
| 2010/0206731 A1 | 8/2010 | Lau et al. |
| 2010/0285514 A1 | 11/2010 | Claussen et al. |
| 2011/0098218 A1 | 4/2011 | Han et al. |
| 2011/0312529 A1 | 12/2011 | He et al. |
| 2012/0228386 A1 | 9/2012 | Wu et al. |
| 2013/0302901 A1 | 11/2013 | Lindsay et al. |
| 2014/0141525 A1 | 5/2014 | Albert et al. |
| 2015/0010935 A1 | 1/2015 | Lindsay et al. |
| 2015/0017655 A1 | 1/2015 | Huang et al. |
| 2015/0086994 A1 | 3/2015 | Williams et al. |
| 2015/0142327 A1 | 5/2015 | Ashcroft et al. |
| 2015/0144506 A1 | 5/2015 | Lindsay et al. |
| 2015/0285818 A1 | 10/2015 | Banala et al. |
| 2015/0362459 A1 | 12/2015 | Chung et al. |
| 2016/0018384 A1 | 1/2016 | Lindsay et al. |
| 2016/0025702 A1 | 1/2016 | Lindsay et al. |
| 2016/0083789 A1 | 3/2016 | Turner et al. |
| 2016/0097759 A1 | 4/2016 | Lindsay et al. |
| 2016/0108002 A1 | 4/2016 | Zhang et al. |
| 2016/0146828 A1 | 5/2016 | Lindsay et al. |
| 2016/0177383 A1 | 6/2016 | Ashcroft et al. |
| 2016/0194698 A1 | 7/2016 | Lindsay |
| 2016/0258925 A1 | 9/2016 | Gyarfas et al. |
| 2016/0280723 A1 | 9/2016 | Zhang et al. |
| 2016/0282295 A1 | 9/2016 | Wang et al. |
| 2017/0038369 A1 | 2/2017 | Lindsay et al. |
| 2017/0044605 A1 | 2/2017 | Merriman et al. |
| 2017/0067902 A1 | 3/2017 | Zhang et al. |
| 2017/0137389 A1 | 5/2017 | Zhang et al. |
| 2017/0168039 A1 | 6/2017 | Lindsay et al. |
| 2017/0276678 A1* | 9/2017 | Ervin ............... G01N 33/48721 |
| 2018/0031549 A1 | 2/2018 | Chen et al. |
| 2018/0073071 A1 | 3/2018 | Ju et al. |
| 2018/0095081 A1 | 4/2018 | Albert et al. |
| 2018/0120286 A1 | 5/2018 | Lindsay et al. |
| 2018/0180567 A1 | 6/2018 | Li et al. |
| 2018/0305727 A1 | 10/2018 | Merriman et al. |
| 2018/0340220 A1 | 11/2018 | Merriman et al. |
| 2019/0004003 A1 | 1/2019 | Merriman et al. |
| 2019/0041355 A1 | 2/2019 | Merriman et al. |
| 2019/0094175 A1 | 3/2019 | Merriman et al. |
| 2019/0112643 A1 | 4/2019 | Aran et al. |
| 2019/0234902 A1 | 8/2019 | Lima, Jr. et al. |
| 2019/0309008 A1 | 10/2019 | Ju et al. |
| 2019/0330695 A1 | 10/2019 | Guo et al. |
| 2020/0157595 A1 | 5/2020 | Merriman et al. |
| 2021/0114025 A1 | 4/2021 | De Freitas Dias et al. |
| 2021/0208127 A1 | 7/2021 | Lindsay et al. |
| 2022/0252542 A1 | 8/2022 | Merriman et al. |

FOREIGN PATENT DOCUMENTS

| | | | |
|---|---|---|---|
| WO | WO 2013/038272 | 3/2013 | |
| WO | WO 2014/074727 | 5/2014 | |
| WO | WO 2015/130781 | 9/2015 | |
| WO | WO 2015/131073 | 9/2015 | |
| WO | WO 2015161119 A1 * | 10/2015 | ............ G01N 33/53 |
| WO | WO 2015/170784 | 11/2015 | |
| WO | WO 2016/161402 | 10/2016 | |
| WO | WO 2016/210386 | 12/2016 | |
| WO | WO 2017/084998 | 5/2017 | |
| WO | WO 2017/123416 | 7/2017 | |
| WO | WO 2017/189930 | 11/2017 | |
| WO | WO 2018/026855 | 2/2018 | |
| WO | WO 2018/132457 | 7/2018 | |
| WO | WO 2018/200687 | 11/2018 | |
| WO | WO 2018/208505 | 11/2018 | |
| WO | WO 2019/046589 | 3/2019 | |
| WO | WO 2019/086305 | 5/2019 | |
| WO | WO 2019/211622 | 11/2019 | |
| WO | WO 2019/217600 | 11/2019 | |
| WO | WO 2019/222527 | 11/2019 | |
| WO | WO 2020/160300 | 8/2020 | |
| WO | WO 2020/243207 | 12/2020 | |
| WO | WO 2020/257654 | 12/2020 | |
| WO | WO 2021/163275 | 8/2021 | |
| WO | WO 2021/173681 | 9/2021 | |
| WO | WO 2021/222791 | 11/2021 | |

OTHER PUBLICATIONS

Lindsay et al., "Recognition tunneling", Nanotechnology 21 (2010) 262001 (12pp) (Year: 2010).*
Extended European Search Report for PCT/US2019031394 dated Jan. 5, 2022. 7 pages.
International Search Report and Written Opinion for PCT/US19/31394 dated Sep. 10, 2019. 11 pages.
Zhang et al., Observation of Giant Conductance Fluctuations in a Protein. Nano Futures. 2017;1(3):035002. 25 pages.
Zhang et al., Role of contacts in long-range protein conductance. Proc Natl Acad Sci U S A. Mar. 26, 2019;116(13):5886-5891.
Ackerman et al., Massively multiplexed nucleic acid detection with Cas13. Nature. Jun. 2020;582(7811):277-282.
Adhikari et al., Conductivity of individual Geobacter pili. RSC Advances, 2016. 6: p. 8354-8357.
Alloway et al., Interface Dipoles Arising from Self-Assembled Monolayers on Gold: UV-Photoemission Studies of Alkanethiols and Partially Fluorinated Alkanethiols. J. Phys. Chem. B 2003, 107:11690-11699.
Altschul et al., Basic local alignment search tool. J Mol Biol. Oct. 5, 1990;215(3):403-10.
Altschul et al., Gapped BLAST and PSI-BLAST: a new generation of protein database search programs. Nucleic Acids Res. Sep. 1, 1997;25(17):3389-402.
Amdursky et al., Electronic transport via proteins. Adv Mater. Nov. 12, 2014;26(42):7142-61.
Amdursky et al., Solid-state electron transport via cytochrome c depends on electronic coupling to electrodes and across the protein. PNAS, Apr. 15, 2014, vol. 111, No. 15, pp. 5556-5561.
Anzai et al., Avidin-biotin complexation for enzyme sensor Applications, Trends in Analytical Chemistry, 1994, 13(5): 205-210.
Artes et al., Transistor-like Behavior of Single Metalloprotein Junctions. Nano Lett.,2012, 12(6), pp. 2679-2684 (publication date (Web): Oct. 5, 2011).

(56) References Cited

OTHER PUBLICATIONS

Aubert et al., Intraprotein radical transfer during photoactivation of DNA photolyase. Nature. Jun. 1, 2000;405(6786):586-90.
Ausubel et al. Current Protocols in Molecular Biology, John Wiley & Sons, New York, 1998. 19 pages.
Barhoumi et al., "Urease immobilization on biotinylated polypyrrole coated ChemFEC devices for urea biosensor development" IRBM, Apr. 1, 2008, 29(2-3): 192-201.
Bostick et al., Protein bioelectronics: a review of what we do and do not know. Rep Prog Phys. Feb. 2018;81(2):026601. 58 pages.
Castellarnau et al., "Integrated microanalytical system based on electrochemical detection and cell positioning" Materials Science and Engineering, 2006, 26: 405-410.
Chang et al., Chemical recognition and binding kinetics in a functionalized tunnel junction. Nanotechnology. Jun. 15, 2012;23(23):235101. 28 pages.
Chen et al., "DNA sequencing using electrical conductance measurements of a DNA polymerase," Nature Nanotechnology, May 5, 2013, pp. 1-7; https://doi.org/10.1038/nnano.2013.71. 7 pages.
Chichil et al., Linkers in the structural biology of protein-protein interactions. Protein Sci. Feb. 2013;22(2):153-67.
Chin et al., Addition of p-Azido-I-phenylalanine to the Genetic Code of *Escherichia coli*. J. Am. Chem. Soc. 2002. 124,31, 9026-9027.
Choi et al. "Site-specific inhibition of integrin alpha v beta 3-vitronectin association by a serasp-val sequence through an Arg-Gly-Asp-binding site of the integrin." Proteomics, vol. 10, Issue 1, No. 1 Jan. 2010, pp. 72-80 (First published Oct. 30, 2009).
Choi et al., "Single-Molecule Lysozyme Dynamics Monitored by an Electronic Circuit," Science (2012) 335:319-324.
Cui et al., Reproducible measurement of single-molecule conductivity. Science. Oct. 19, 2001;294(5542):571-4.
Cui et al: "Layer-by-layer 1 assembly of multilayer filme composed of avidin and biotin-labeled antibody for immunosensing", Biosensors And Bioelectronics, Jan. 1, 2003, 18(1): 59-67.
Dellafiore et al., Modified Nucleoside Triphosphates for In-vitro Selection Techniques. Front Chem. May 4, 2016;4:18.
Duffy et al., Modified nucleic acids: replication, evolution, and next-generation therapeutics. BMC Biology, Sep. 2, 2020. 18:112. 14 pages.
Fairhead et al., Plug-and-play pairing via defined divalent streptavidins. J Mol Biol. Jan. 9, 2014;426(1):199-214.
Fujino et al, Chimeric RNA Oligonucleotides Incorporating Triazole-Linked Trinucleotides: Synthesis and Function as mRNA in Cell-Free Translation Reactions. J Org Chem. Oct. 7, 2016;81(19):8967-8976.
Fulton et al., Purification of monoclonal antibody against Ebola GP1 protein expressed in Nicotiana benthamiana. J Chromatogr A. Apr. 10, 2015;1389:128-32.
Garg et al., Interface Electrostatics Dictates the Electron Transport via Bioelectronic Junctions. ACS Appl Mater Interfaces. Dec. 5, 2018;10(48):41599-41607.
Giese et al., Direct observation of hole transfer through DNA by hopping between adenine bases and by tunnelling. Nature. Jul. 19, 2001;412(6844):318-20.
Giese et al., Long distance charge transport through DNA: quantification and extension of the hopping model. Chemphyschem. Dec. 15, 2000;1(4):195-8.
Gonnet et al., Exhaustive matching of the entire protein sequence database. Science. Jun. 5, 1992;256(5062):1443-5.
Guo et al., Tuning electronic transport via hepta-alanine peptides junction by tryptophan doping. Proc Natl Acad Sci U S A. Sep. 27, 2016;113(39):10785-90.
Hajian et al., Detection of unamplified target genes via CRISPR-Cas9 immobilized on a graphene field-effect transistor. Nat Biomed Eng. Jun. 2019;3(6):427-437.
Harriman. Further comments on the redox potentials of tryptophan and tyrosine. Journal of Physical Chemistry 1987. 91:6102-6104.
Hays et al., Development of capacitance based immunosensors on mixed self-assembled monolayers. Sensors and Actuators B: Chemical, Apr. 26, 2006, vol. 114, No. 2, pp. 1064-1070.
Hohl et al. Engineering a Polyspecific Pyrrolysyl-tRNA Synthetase by a High Throughput FACS Screen. Sci Rep. Aug. 19, 2019;9(1):11971.
Hozel et al., "Trapping Single Molecules by Dielectrophoresis" Physical Review Letters, 2005, 128102-1-4.
Ihalainene et al., "Application of paper-supported printed gold eletrodes for impedimetric immunosensor development" Biosensors 2013, 3:1-17.
Jeffrey, An Introduction to Hydrogen Bonding. Oxford University Press New York. 1997. TOC only. 6 pages.
Kluenker et al., Monitoring Thiol-Ligand exchange on Au nanoparticle surfaces. Langmuir. Jan. 30, 2018;34(4):1700-1710.
Kotlowski Fine discrimination of volatile compounds by graphene-immobilized odorant-binding proteins, Sensors and Actuatores B: Chemical 2018 (256): 564-72.
Krishnan et al., "Long-Range Conductivity in Proteins Mediated by Aromatic Residues" ACS Phys. Chem Au 2023, 3:444-455.
Kyte et al., A simple method for displaying the hydropathic character of a protein. J Mol Biol. May 5, 1982;157(1):105-32.
Lagunas et al., Long distance electron transfer through the aqueous solution between redox partner proteins. Nat Commun. Dec. 4, 2018;9(1):5157.
Lai et al., Monoclonal antibody produced in plants efficiently treats West Nile virus infection in mice. Proc Natl Acad Sci U S A. Feb. 9, 2010;107(6):2419-24.
Lai et al., Robust production of virus-like particles and monoclonal antibodies with geminiviral replicon vectors in lettuce. Plant Biotechnol J. Jan. 2012;10(1):95-104.
Leary et al., Unambiguous one-molecule conductance measurements under ambient conditions. Nano Lett. Jun. 8, 2011;11(6):2236-41.
Li et al., CRISPR-SE: a brute force search engine for CRISPR design. NAR Genom Bioinform. Feb. 23, 2021;3(1):lqab013.
Li et al., Synthesis and Photovoltaic effect on electron-withdrawing units for low band gap conjugated polymers bearing bi(thienylenevinylene) side chains. Polymers. 2019, vol. 11 iss 9 pp. 1-13.
Lindsay. Ubiquitous Electron Transport in Non-Electron Transfer Proteins. Life (Basel). May 20, 2020;10(5):72. 13 pages.
Liu et al., Vertical T cellimmunodomincance and epitope entropy determine HIV-1 escape. J Clin Invest. Jan. 2013;123(1):380-93.
Maalouf et al., Label-Free Detection of Bacteria by Electrochemical Impedance Spectroscopy: Comparison to Surface Plasmon Resonance. Anal. Chem, May 25, 2007, vol. 79, No. 13, pp. 4879-4886.
Main et al., Design of stable alpha-helical arrays from an idealized TPR motif. Structure. May 2003;11(5):497-508.
Malvankar et al., Tunable metallic-like conductivity in microbial nanowire networks. Nat Nanotechnol. Aug. 7, 2011;6(9):573-9.
Marakova et al., An updated evolutionary classification of CRISPR-Cas systems. Nat Rev Microbiol. Nov. 2015;13(11):722-36.
McKenzie et al., Recent progress in non-native nucleic acid modifications. Chem Soc Rev. Apr. 26, 2021;50(8):5126-5164.
Mejias et al., Controlled nanometric fibers of self-assembled designed protein scaffolds. Nanoscale. Oct. 7, 2014;6(19):10982-8.
Metsky et al., Diagnostic design with machine learning model-based optimization. bioRxiv 2020.11.28.401877: 95 pages.
Mullegama et al., Nucleic Acid Extraction from Human Biological Samples. Methods Mol Biol 2019;1897:359-383.
Nitzan. Chemical dynamics in condensed phases. Oxford University Press., Oxford. 2006. TOC only. 13 pages.
Odella et al., Controlling Proton-Coupled Electron Transfer in Bioinspired Artificial Photosynthetic Relays. J Am Chem Soc. Nov. 14, 2018;140(45): 15450-15460.
Olsen et al., "Electronic Measurements of Single-Molecule Processing by DNA Polymerase I (Klenow Fragment)," Journal of the American Chemical Society (Apr. 30, 2013); pp. 1-12; DOI:10.1021/ja311603r.
Ouerghi et al., "Impedimetric immunosensor using avidin-biotin for antibody immobilization" Bioelectrochemistry, May 15, 2002, 56(1-2):131-133.

(56) References Cited

OTHER PUBLICATIONS

Pang et al. "Fixed-Gap Tunnel Junction for Reading DNA Nucleotides" ACS Nano, 2014, 8(12), pp. 11994-12003 (Publication Date (Web): Nov. 7, 2014).

Pearson. Using the FASTA program to search protein and DNA sequence databases. Methods Mol Biol. 1994;24:307-31.

Prodromids et al., "Impedimetric immunosensors—A review" Electrochimica Acta, May 30, 2010, 55(14): 4227-4233.

Quast et al., Cotranslational incorporation of non-standard amino acids using cell-free protein synthesis. FEBS Lett. Jul. 8, 2015;589(15):1703-12.

Ruiz et al., Bioengineering a Single-Protein Junction. J Am Chem Soc. Nov. 1, 2017;139(43):15337-15346.

Sambrook et al., Molecular Cloning: A Laboratory Manual, 3d ed., Cold Spring Harbor Press, 2001. TOC only. 23 pages.

Sano et al., Cooperative biotin binding by streptavidin. Electrophoretic behavior and subunit association of streptavidin in the presence of 6 M urea. J Biol Chem. Feb. 25, 1990;265(6):3369-73.

Seifert, Characterization of Streptavidin Binding to Biotinylated, Binary Self-Assembled Thio Monolayers-Influence of Component Ratio and Solvent, Langmuir, 2010, 26(9): 6386-93.

Sek et al., Conductance of alpha-helical peptides trapped within molecular junctions. J Phys Chem B. Oct. 5, 2006;110(39):19671-7.

Sequences of amino acids as found on the world wide web at bmrb.wisc.edu/referenc/choufas. 4 pages.

Shimura & Yoshida, "Heterogeneous photocatalytic hydrogen production from water and biomass derivatives" Energy Environmental Science 2011, 4: 2467.

Smith. The hydrophilic nature of a clean gold surface. J. Colloid Interface Science 1980. 75:51-55.

Staals et al., RNA targeting by the type III-A CRISPR-Cas Csm complex of Thermus thermophilus. Mol Cell. Nov. 20, 2014;56(4):518-30.

Tripkovic et al., Standard hydrogen electrode and potential of zero charge in density functional calculations. Phys. Rev. B 2011. 84:115452.

Tuchband et al., Insulated gold scanning tunneling microscopy probes for recognition tunneling in an aqueous environment. Rev Sci Instrum. Jan. 2012;83(1):015102.

Vaish et al., A novel, modification-dependent ATP-binding aptamer selected from an RNA library incorporating a cationic functionality. Biochemistry. Jul. 29, 2003;42(29):8842-51.

Varga et al., "Binding of a Mouse Monoclonal IgE (anti-DNP) antibody to radio-derivatized polystyrene-DNP complexes" The FASEB Journal, Federation of American Societies for Experimental Biology, Jun. 1, 1990, 4(9): 2678-2683.

Vattay et al., Quantum Criticality at the Origin of Life. Journal of Physics: Conference Series 2015. 626: p. 012023. 11 pages.

Willner et al., Mediated electron transfer in glutathione reductase organized in self-assembled monolayers on Au electrodes. J. Am. Chem. Soc., 1992. 114: p. 10965-10966.

Xiao et al., Conductance titration of single-peptide molecules. J Am Chem Soc. May 5, 2004;126(17):5370-1.

Yang et al., Plant-produced Zika virus envelope protein elicits neutralizing immune responses that correlate with protective immunity against Zika virus in mice. Plant Biotechnol J. Feb. 2018;16(2):572-580.

Yoon, "Hidden Markov Models and their Applications in Biological Sequence Analysis" Current Genomics, 2009, 10:402-415.

Zhang et al., Electronic Conductance Resonance in Non-Redox-Active Proteins. J Am Chem Soc. Apr. 1, 2020;142(13):6432-6438.

Zhang et al., Electronic Decay Length in a Protein Molecule. Nano Lett. Jun. 12, 2019;19(6):4017-4022.

Zhang et al., Engineering an Enzyme for Direct Electrical Monitoring of Activity. ACS Nano. Feb. 25, 2020;14(2):1360-1368.

Zwolak et al. "Electronic Signature of DNA Nucleotides via Transverse Transport" NanoLett., 2005, 5(3), pp. 421-424 (Publication Date (Web): Feb. 12, 2005).

\* cited by examiner

METHOD FOR ELECTRONIC DETECTION AND QUANTIFICATION OF ANTIBODIES

FEDERALLY SPONSORED RESEARCH OR DEVELOPMENT

This invention was made with government support under HG009180 awarded by the National Institutes of Health. The government has certain rights in the invention.

BACKGROUND

Known methods for analyzing the antibody content in a sample (e.g., a blood sample) is carried out using fluorescently labeled secondary antibodies that bind to the stem or constant region of the target antibody (which in turn binds its epitope on a bead or array). These methods have several disadvantages, such as, low sensitivity, single molecule detection is very difficult, and the contrast is poor. In addition, large, and fragile, optical imaging devices are needed and unfortunately, they are not easily deployed in the field or in third world countries. Thus, there remains a need for a compact, rugged high-sensitivity and high selectivity antibody detector. Such a detector would have important applications in the clinic, where, for example, antibodies to non-surface-coat HPV proteins serve as an early indicator of cancer. Much earlier detection of highly infectious diseases (like Ebola) would enable control of their spread. Monitoring binding to a large enough array of peptides could even signal the pre-symptomatic onset of infection by an unknown pathogen.

It has been shown that protein binding to a ligand can be detected via electronic signals that are induced when the protein is captured by a ligand attached to a closely spaced pair of electrodes. See, e.g., US 2018/0120286. FIG. 1 shows a known single molecule sensing device in which peptide ligand 74 for a target protein 75 is attached to electrodes 73 and 71. The gap, d is chosen to be no more than twice the length of the ligand, L1, plus the length of the protein L2, and no less than 2L1. When a protein binds the electrode, and a bias applied across the electrodes exceeds 100 mV, large fluctuations in current are observed. These fluctuations signal the binding of the target protein.

The devices of US 2018/0120286 can detect single molecule binding events. However, they cannot quantify the amount of target protein in a sample.

Citation of any reference in this section is not to be construed as an admission that such reference is prior art to the present disclosure.

SUMMARY

The present disclosure provides a sensing device and methods for detecting, and quantifying the amount of, a target protein in a sample.

Devices and methods for detecting a protein or antibody in a sample are provided. In some embodiments, a device is provided, the device comprising: a first and a second electrode, the first and second electrode being separated by a gap; a first ligand attached to the first electrode and a second ligand attached to the second electrode; wherein a detectable signal is produced when the protein/antibody interacts with the first and second ligand.

In some embodiments, the device comprises: a first and a second electrode, the first and second electrode being separated by a gap and comprising an opening formed therethrough; wherein: a plurality of ligands is attached to at least one of the first electrode and the second electrode; the ligand has a length L1 and is capable of binding a target protein having a length L2; and the width of the gap is no less than 2L1 and no more than 2L1+L2.

In some embodiments, the target protein is an antibody of interest. In some embodiments, the target protein is integrin. In some embodiments, the antibody is selected from the group consisting of IgE Anti-DNP, IgG Anti-HIV and IgG Anti-Ebola.

In some embodiments, the first and/or second electrode comprise palladium.

In some embodiments, the first and/or second electrode comprise platinum.

In some embodiments, the first and second ligand are the same. In some embodiments, the first and second ligand are a ligand/epitope specific to the protein/antibody of interest.

In some embodiments, the first and second ligand are selected from the group consisting of RGD, thiolated-dinitrophenol, CHNTPVYKLDISEATQV and CALDR-WEKIRLR.

In some embodiments, the first and second ligand are proteins comprising surface thiols. The surface thiols can be naturally present or introduced via modifications known in the art. The surface thiols attach the protein ligand to the electrodes.

In some embodiments, the gap has a width of about 1.0 nm to about 10.0 nm. In some embodiments, the gap has a width of about 1.0 nm to about 7.5 nm. In some embodiments, the gap has a width of about 1.0 nm to about 5.0 nm.

In some embodiments, the sensing device detects a single molecule. In other embodiments, the sensing device detects a plurality of molecules.

In some embodiments, the sensing device further comprises a detector for measuring a signal produced when the target protein binds the ligand.

In some embodiments, the sensing device further comprises a system for introducing and removing buffer and sample.

In some embodiments, the sensing device further comprises a system for analyzing the signal produced when the target protein binds the ligand.

In some embodiments, the methods are provided, the method comprising (a) providing a sensing device as described herein; (b) contacting the first electrode and the second electrode with a sample comprising a protein/antibody of interest; (c) detecting the signal produced when the protein/antibody interacts with the first and second ligand attached to the first and second electrodes, wherein the detectable signal indicates the presence of a protein/antibody.

In some embodiments, a method of detecting the presence of a protein/antibody in a sensing device is provided, the method comprising: (a) recording a current when a sample suspected of comprising a target protein is in contact with the sensing device, as described herein; and (b) determining that the protein/antibody is present by detecting an increase in current.

The methods can be used to quantify the concentration of the protein/antibody of interest by means of an electrical readout of binding kinetics.

In some embodiments, a method of determining the concentration of a target protein in a sample is provided, the method comprising: (a) recording the time course of current when a sample suspected of comprising a protein/antibody is in contact with a sensing device, as described herein; and (b) determining the concentration of protein/antibody from the time course of current.

The methods provide for direct, label-free electronic detection and quantification of protein/antibody concentration with high specificity and sensitivity.

DETAILED DESCRIPTION

Figure 1:
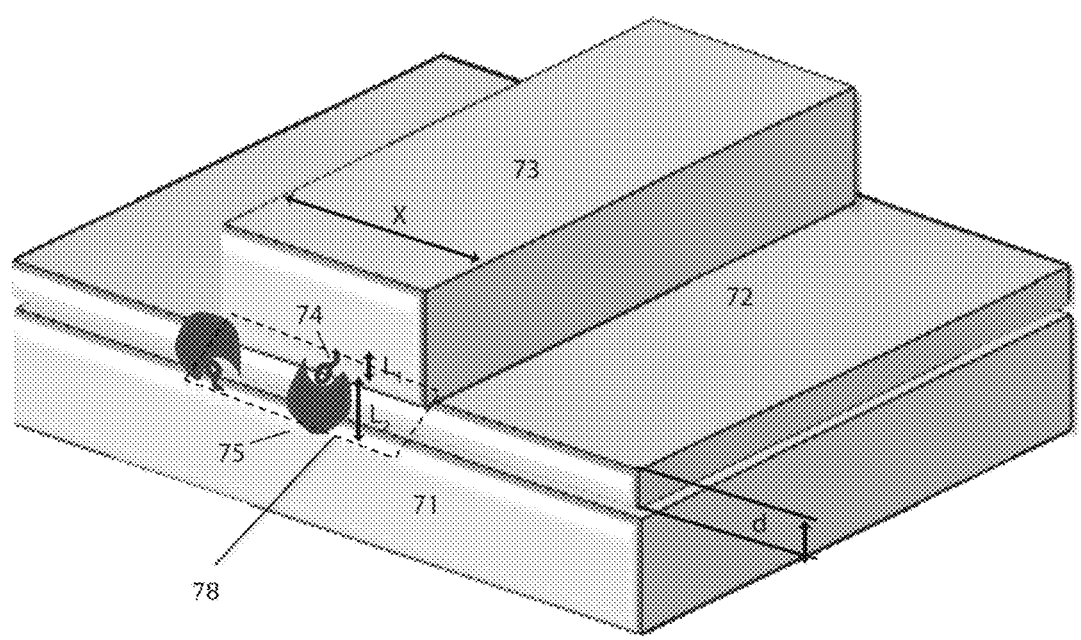
FIG. 1 shows a cross-sectional view of a known single molecule sensing device.

The invention includes at least the following:

(1.) A method for detecting a protein substantially as shown and described.

(2.) A method for quantifying a protein substantially as shown and described.

(3.) A method for detecting an antibody substantially as shown and described.

(4.) A method for quantifying an antibody substantially as shown and described.

(5.) A sensing device substantially as shown and described.

(6.) A sensing device comprising:
a first and a second electrode, the first and second electrode being separated by a gap and comprising an opening formed therethrough;
wherein:
a plurality of ligands is attached to at least one of the first electrode and the second electrode;
the ligand has a length L1 and binds a target protein having a length L2; and
the width of the gap is no less than 2L1 and no more than 2L1+L2.

(7.) The sensing device of the above (6.), wherein the first and/or second electrode comprise palladium.

(8.) The sensing device of the above (6.), wherein the plurality of ligands is an epitope specific to the target protein.

(9.) The sensing device of the above (6.), the sensing device further comprising a detector for measuring the signal produced when the target protein binds the ligand.

(10.) The sensing device of the above (6.), further comprising a system for introducing and removing buffer and sample.

(11.) The sensing device of the above (6.), further comprising a system for analyzing the signal produced when the target protein binds the ligand.

(12.) A method of detecting the presence of a protein/antibody in a sensing device, the method comprising:
(a) recording a current when a sample suspected of comprising a target protein is in contact with the sensing device, wherein
the sensing device comprises:
a first and a second electrode, the first and second electrode being separated by a gap and comprising an opening formed therethrough;
wherein:
a plurality of ligands is attached to at least one of the first electrode and the second electrode;
the ligand has a length L1 and binds a target protein having a length L2; and
the width of the gap is no less than 2L1 and no more than 2L1+L2;
a detector for measuring the current produced when the target protein binds the ligand; and
(b) determining that the protein/antibody is present by detecting an increase in current.

(13.) A method of determining the concentration of a target protein in a sample, the method comprising:
(a) recording the time course of current when a sample suspected of comprising a protein/antibody is in contact with a sensing device, wherein
the sensing device comprises:
a first and a second electrode, the first and second electrode being separated by a gap and comprising an opening formed therethrough;
wherein:
a plurality of ligands is attached to at least one of the first electrode and the second electrode;
the ligand has a length L1 and binds a target protein having a length L2; and
the width of the gap is no less than 2L1 and no more than 2L1+L2; and
a detector for measuring the current produced when the target protein binds the ligand; and
(b) determining the concentration of protein/antibody from the time course of current.

Definitions

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The term "antibody" as used herein includes whole antibodies, monoclonal antibodies, polyclonal antibodies, monospecific antibodies, multispecific antibodies (e.g., bispecific antibodies), and antibody fragments that exhibit biological activity. An antibody may be of any type or class (e.g., IgG, IgE, IgM, IgD, and IgA) or subclass (e.g., IgG1, IgG2, IgG3, IgG4, IgA1 and IgA2). The antibody may be derived from any suitable species. In some embodiments, the antibody is of human or murine origin. An antibody may be, for example, human, humanized or chimeric.

The term "sample" as used herein refers to a biological sample and includes blood serum extracted from blood, urine, sputum or any other source of biomarker proteins, including those extracted and purified from a sample obtained from a patient.

Although the invention has been described and illustrated in the foregoing illustrative embodiments, it is understood that the present disclosure has been made only by way of example, and that numerous changes in the details of implementation of the invention can be made without departing from the spirit and scope of the invention. Features of the disclosed embodiments can be combined and rearranged in various ways. All publications, patents and other documents mentioned herein are incorporated by reference in their entirety.

Sensing Devices for Quantifying Protein Concentration

The present disclosure provides sensing devices for quantifying protein concentration in a sample.

Figure 2:
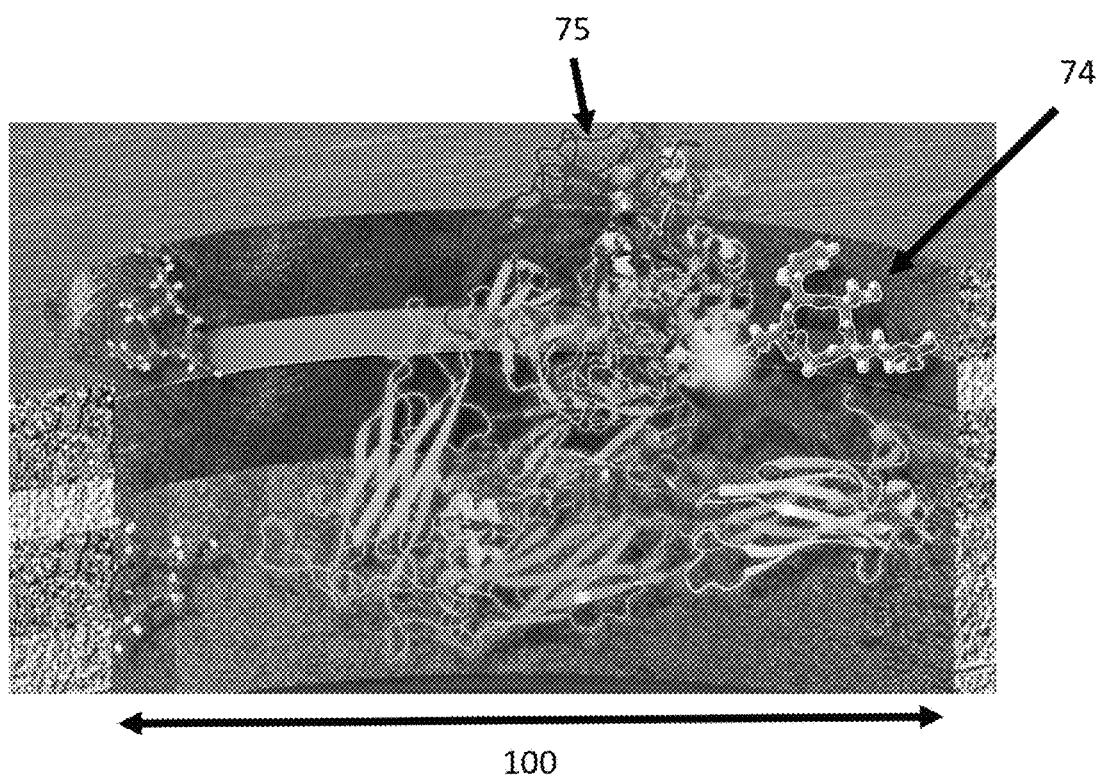
FIG. 2 shows an opening made in the known device of FIG. 1 such that only one protein molecule can interact with the electrodes.

Known sensing devices, such as that depicted in FIG. 1, can sense when a single molecule binds a closely-spaced pair of electrodes. These measurements were obtained by making an opening in the sensing device of FIG. 1 that was small enough to allow only one protein molecule to approach in close proximity to the electrodes, as illustrated in FIG. 2. FIG. 2 shows that the diameter of the opening 100 is chosen to be only just larger than the size of the target protein 75 so that when a first protein binds one of the peptide ligands 74, there is no space for a second protein to bind. In another improvement over known devices (e.g., Zhang, B.; Song, W.; Pang, P.; Zhao, Y.; Zhang, P.; Csabai, I.; Vattay, G.; Lindsay, S. *Nano Futures* 2017, 1, (3).), passivation of the device has reduced background leakage currents to negligible amounts, so the full-current voltage relationship can be recorded, particularly in the low bias range (below 100 mV). With poor passivation, device leakage currents obscure the signal owing to the protein binding, so it only becomes evident when going to a bias large enough to drive distinctive fluctuations in the protein. Thus, it is desirable to access the current caused just by protein binding over the whole current range. However, the distinctive fluctuations observed at a bias greater than 100 mV can be very useful, because they provide a method for counting the number of proteins that are bound. If only one protein is bound, then the fluctuations in current (above 100 mV bias) occur between two distinct levels, as can be observed by setting the bias to, for example, 200 mV and recording current as a function of time. If two molecules are trapped, the signals are superimposed giving rise to three distinct levels of current. Three molecules will give four levels and so on.

Figure 3:
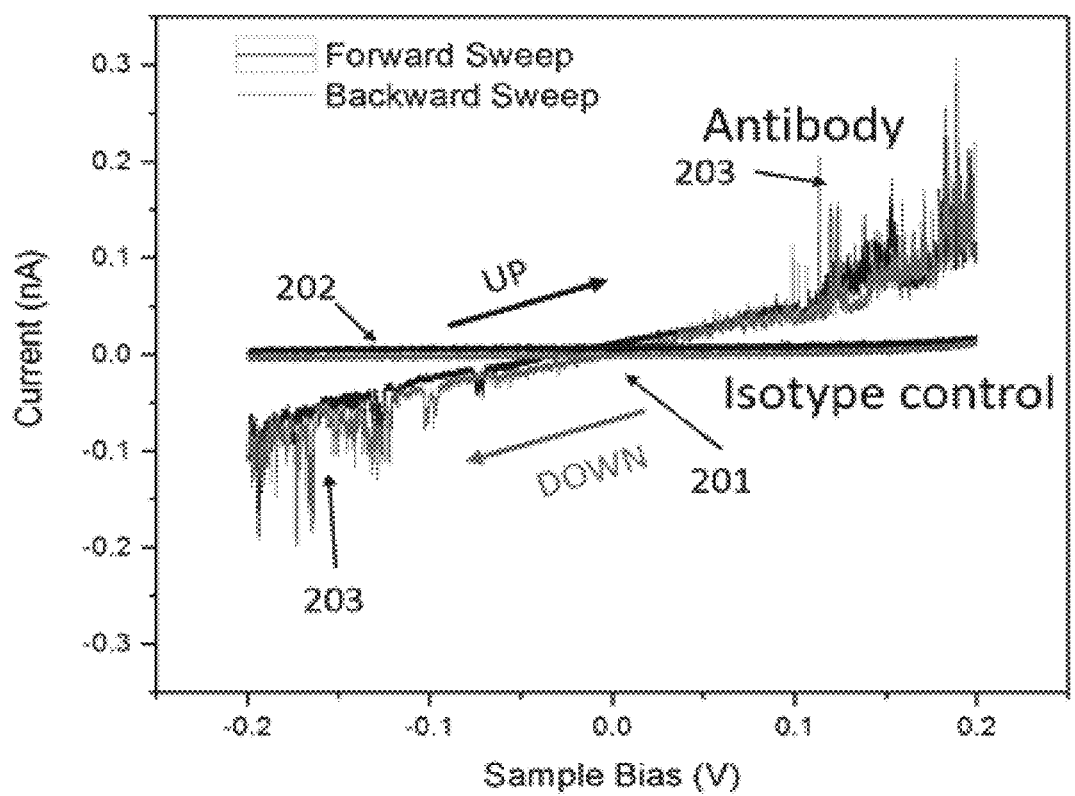
FIG. 3 shows a typical current vs. voltage response recorded for a single protein molecule.

FIG. 3 provides a representative curve for all the proteins described herein. FIG. 3 shows that the electrical response at low bias 201 is linear (Ohmic). When control experiments are carried out with proteins or antibodies that do not specifically bind the peptide ligand, no signal is detected at all 202. The current fluctuations that were previously observed are still observed here, but again, only above about ±100 mV bias 203.

The slope of the curve, di/dV in the low bias region 201 yields the conductance G of a single molecule. Table 1 provides antibody-epitope pairs for which single molecule conductance has been measured.

TABLE 1

| Antibody | Epitope | $K_D$ | Control |
|---|---|---|---|
| IgE Anti-DNP | Thiolated-dinitrophenol | 65 nM | IgE isotype |
| IgG Anti-HIV | CHNTPVYKLDISEATQV | 240 nM | IgG isotype |
| IgG Anti-Ebola | CALDRWEKIRLR | 1400 nM | IgG isotype |

Figure 4:
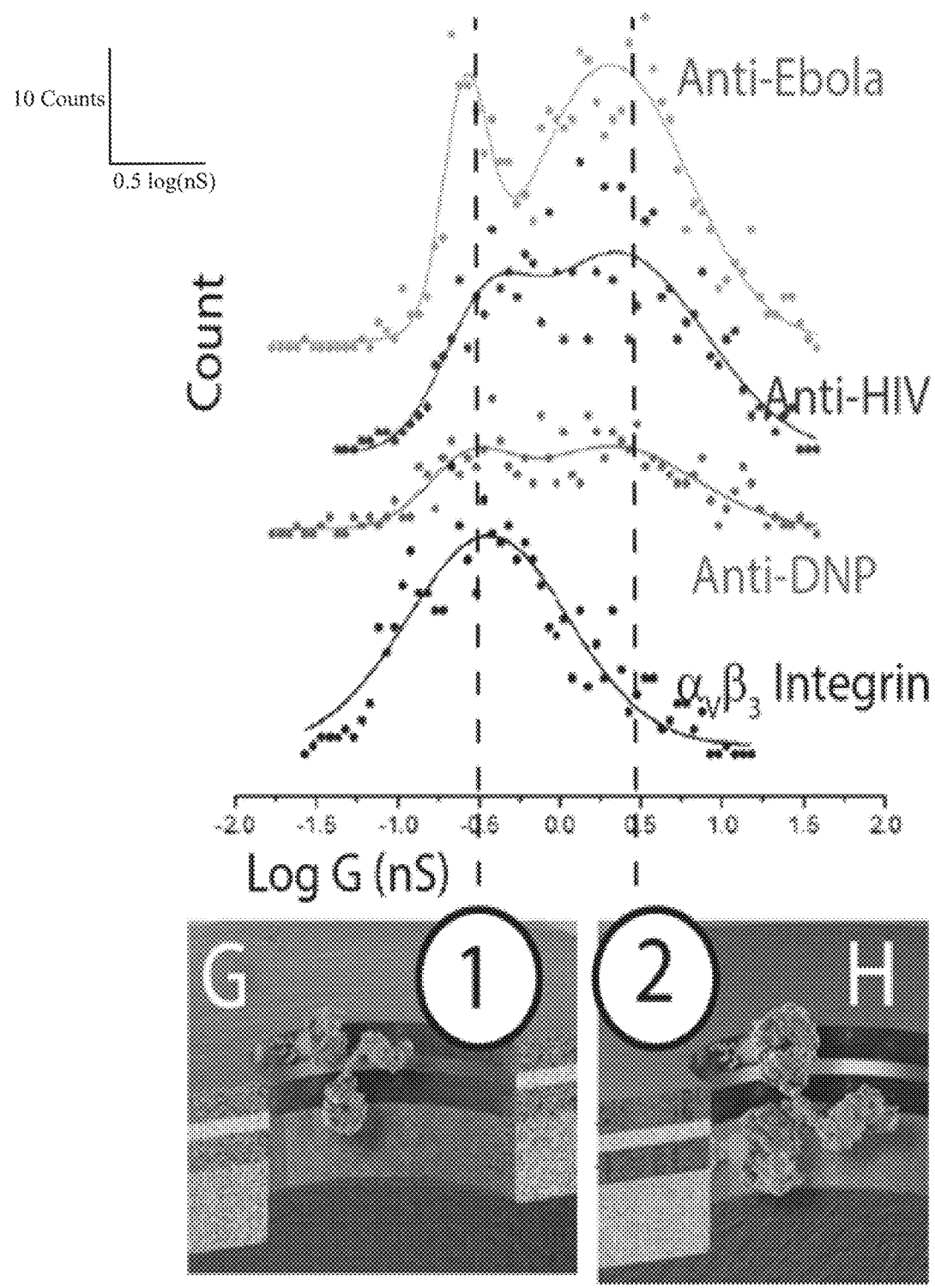
FIG. 4 shows the distributions of single-molecule conductance for (top) an anti-Ebola antibody binding its epitope, (next down) an anti-HIV antibody binding its epitope, (next down) an anti-DNP antibody binding its epitope, and (bottom) $\alpha v\beta_3$ integrin binding RGD peptide. The antibodies can bind to a single electrode (G) or across both (H).

The distributions of conductance G, measured for single molecules of each antibody and the protein integrin as calculated from the slopes 201 of the current-voltage plots (e.g., FIG. 3) are shown in FIG. 4. In these plots, the distributions are plotted vs. log(G). The distributions for the three antibodies peak at about log(G)=−0.5 (G=0.3 nS) and +0.5 (3 nS). Integrin, which only has one ligand binding site has a single peak in the distribution at 0.3 nS. These data show clearly that single molecules are being measured, because the spread in data resulting from the capture of multiple molecules would obscure this relationship between the number of binding sites and the number of peaks in the current distributions. They further show that the conductance of these molecules does not depend strongly on binding strength, which for these three antibodies (Table 1) differs by a factor of 20 (as measured by the dissociation constant, $K_D$).

Figure 5:
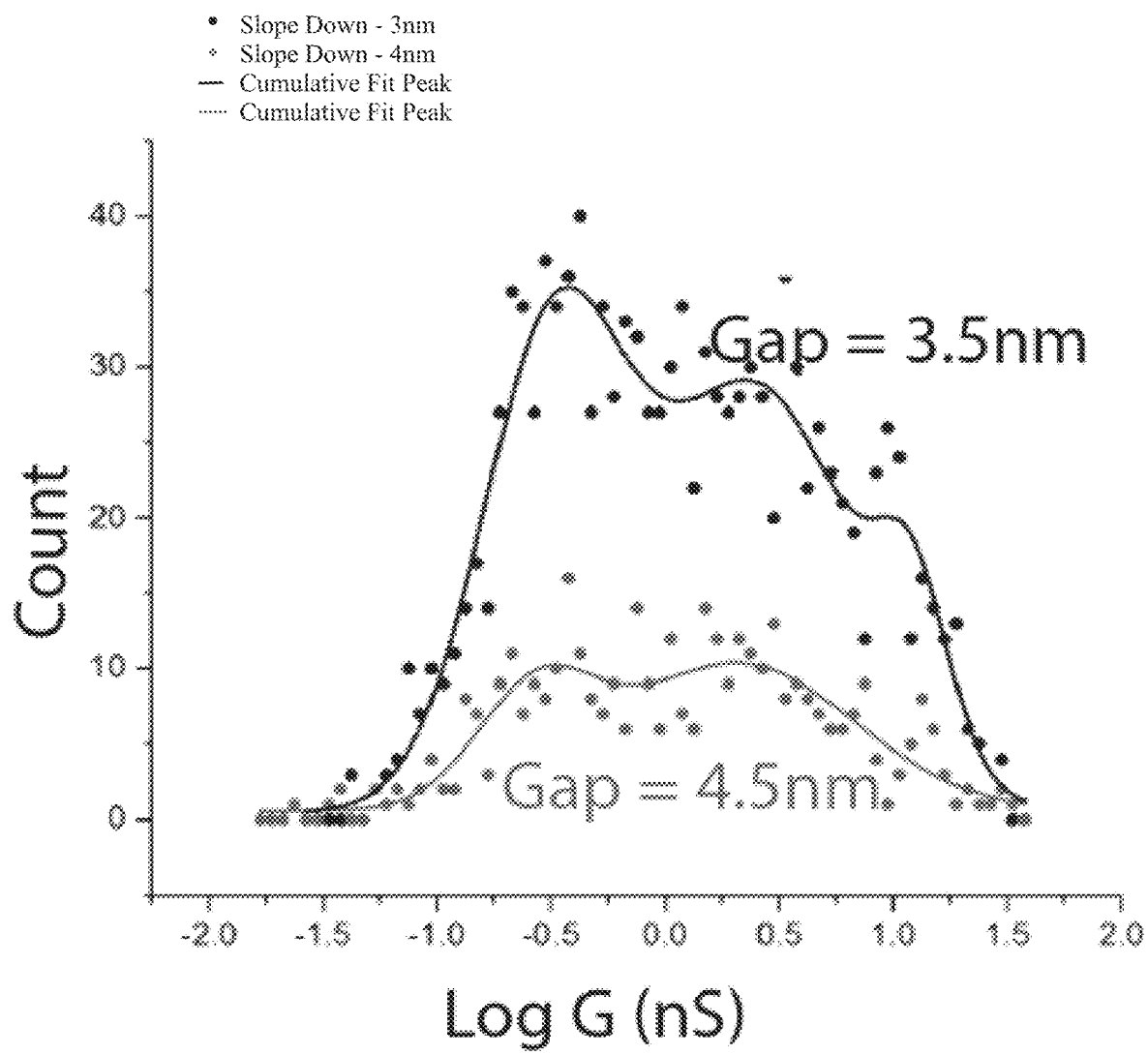
FIG. 5 shows that current through an antibody is relatively insensitive to the gap between electrodes.

FIG. 5 shows that the currents are themselves quite insensitive to the gap size in the devices, so long as the bound antibody can span the gap. FIG. 5 shows current distributions for the anti-DNP binding DNP as obtained at gaps of 3.5 and 4.5 nm. Once again, the peaks in the distribution appear at about G=0.3 and G=3 nS.

This sensing device reliably reports on the number of single molecules bound, because each contributes about the same amount of current, and whether or not the gap can be bridged by a single molecule with multiple binding sites. Furthermore, because the ligand binding is what is being used to sense current, the contrast is enormous. No non-specific interactions were recorded in over 1000 trails with a non-binding isotype (Table 1). About 30% of all recordings yielded a positive signal in the presence of the target antibody.

These measurements were taken with antibody (and control) solutions in the nM concentration range, and many minutes were required for a signal to be observed at the lower end of the concentration range. This is a consequence of the small electrode area in these devices designed to capture a single molecule. A second consequence of this design is that the output is binary: a molecule is bound (signal) or not (no signal).

Accordingly, the present disclosure provides a sensing device that increases sensitivity and can quantify antibody concentration. The sensing device comprises: a first and a second electrode, the first and second electrode being separated by a gap and comprising an opening formed therethrough; wherein: a plurality of ligands is attached to at least one of the first electrode and the second electrode; the ligand has a length L1 and is capable of binding a target protein having a length L2; and the width of the gap is no less than 2L1 and no more than 2L1+L2.

Figure 6:
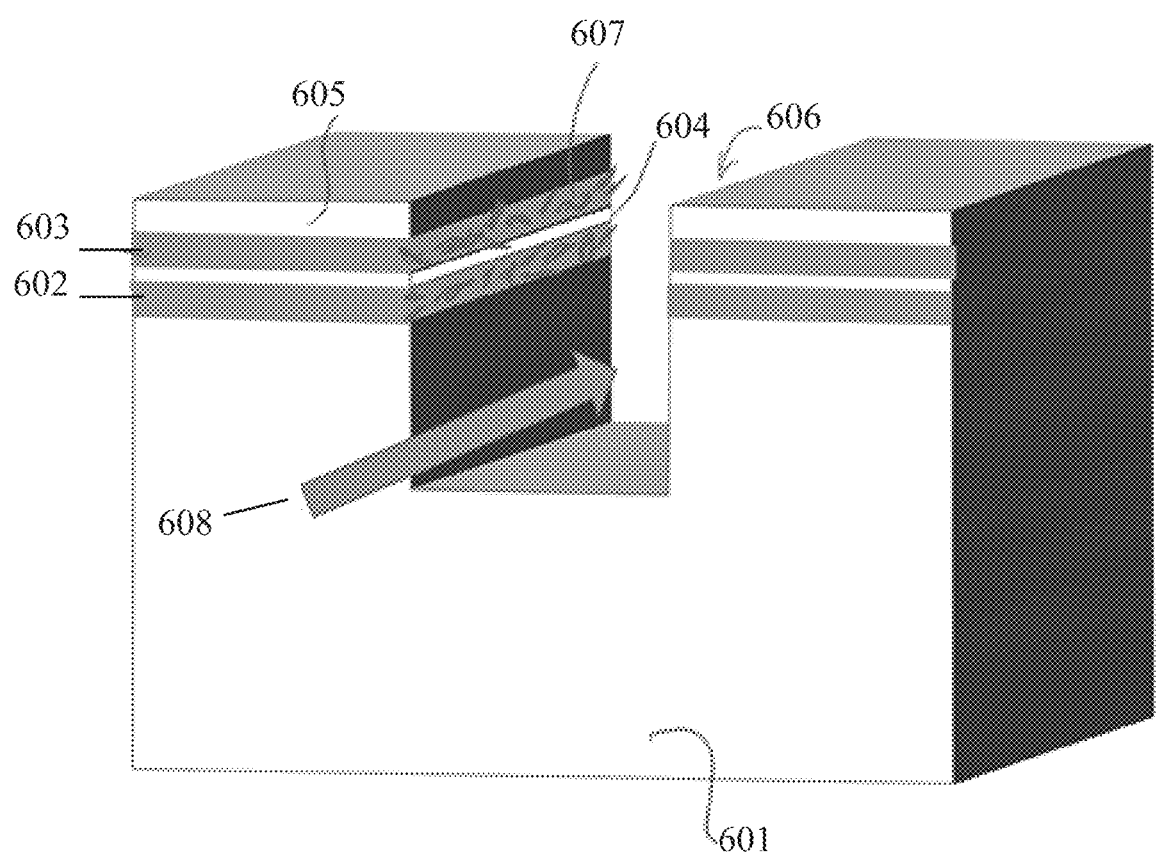
FIG. 6 shows a sensing device according to an embodiment of the present disclosure, in which a sample comprising a target protein is passed through a channel bounded by electrode pairs functionalized with a plurality of ligands.

FIG. 6 shows a sensing device according to one embodiment of the disclosure. The device comprises a first and a second electrode 602, 603 separated by a dielectric layer 604 no thicker than twice the epitope length (2×L1) plus the target molecule length (L2), and no thinner than 2L1. A passivating layer of a dielectric, such as $SiO_2$ or $Al_2O_3$, is placed over the top electrode to isolate it from an electrolyte solution and an opening 606 milled down into the device using reactive ion etching (RIE). The opening passes through the electrode assembly and penetrates some way into the underlying silicon substrate 601. This permits fluid flow 608 of sample solution past the electrodes. The electrodes are, in turn, functionalized with a plurality of ligands 604. The amount of ligand attached to the electrodes will increase with the length of the electrodes. For the single molecule data, the length of the electrode was 1 to 50 nm. If the length of the electrodes is increased to about 5 microns, then the sensitivity of the device will be reduced to about 1 nM (instantaneous response) or to the pM range by waiting ~minutes for a signal.

The present disclosure provides an array of sensing devices. The array comprises an arrangement of a plurality of sensing devices on a surface, e.g., a silicon wafer. Each device can be separately functionalized with a given ligand, so that the array can test for the presence of many different proteins/antibodies in one run.

Methods of Using the Sensing Devices

The present disclosure provides a method of detecting a protein/antibody in a sensing device as herein described. The present disclosure also provides a method of determining the concentration of a protein/antibody in a sample using a sensing device as herein described.

Figure 7:
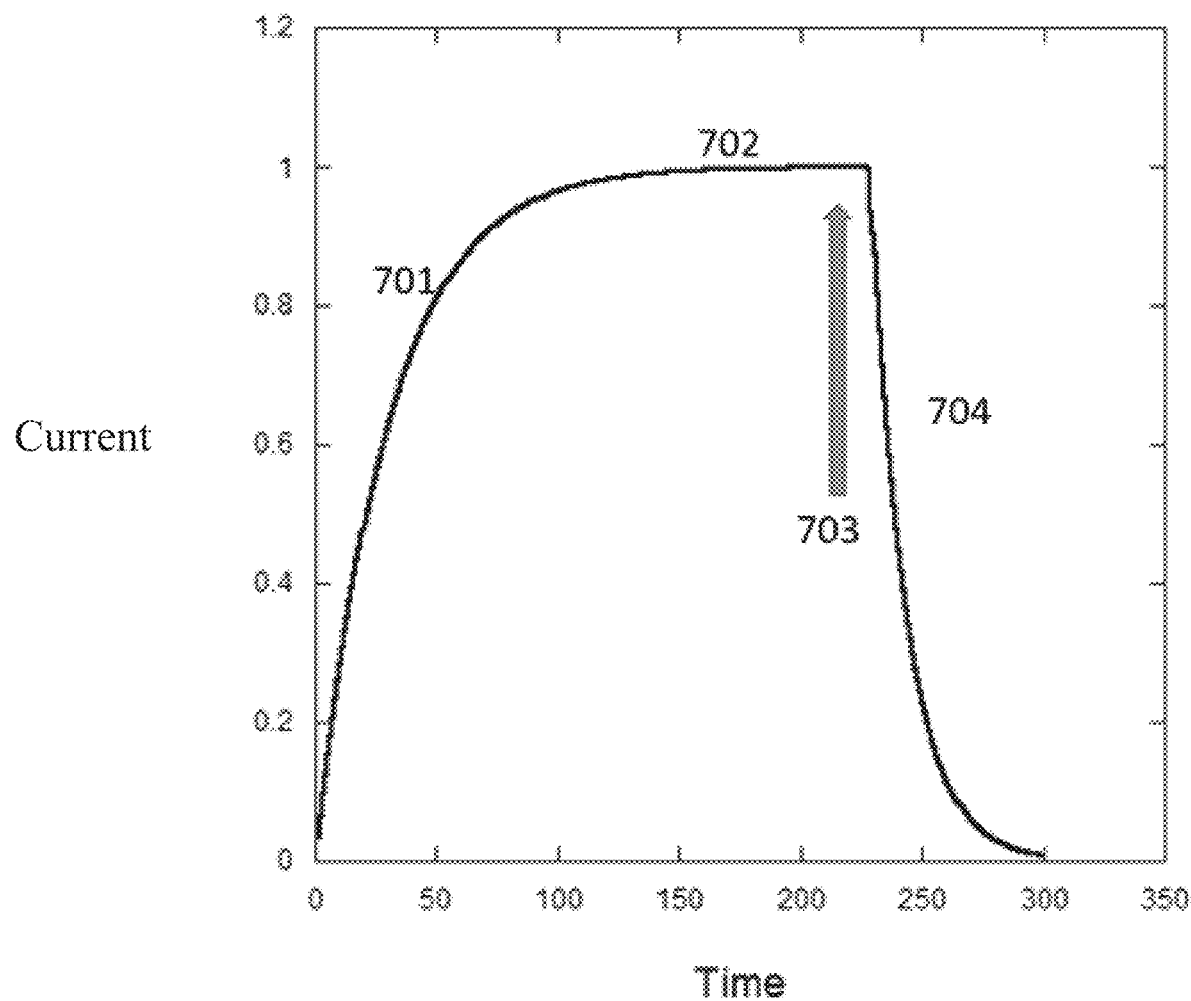
FIG. 7 shows the quantification of antibody concentration from the binding and unbinding kinetics measured via a plot of device current vs. time.

Because the sensing device comprises a plurality of ligands 604 attached to at least one of the first electrode and the second electrode, and with the knowledge that the current increases by a relatively fixed amount for a binding event at each binding site, the time course of current on exposure to a solution of protein/antibody will follow the usual association kinetics (702 in FIG. 7). This increase in current depends on both the concentration of ligand on the electrodes and the concentration of protein/antibody in the sample as well as the association and dissociation rates for the binding. A steady-state current, $i_e$, 702 is reached when, at a given concentration, the association and dissociation rates are equal. At this point $$i_e = i_{max} \frac{C}{C + k_d}, \quad (1)$$

where C is the concentration of protein/antibody, $i_{max}$ is the current measured when the electrodes are fully saturated and $K_D$ the dissociation constant. Thus, the concentration can be measured directly from current in equilibrium. If $K_D$ is unknown, it can be determined from the off-rate, $K_{off}$ determined by rinsing 703 the device with protein-free buffer and measuring the decay of current 704. This yields $K_{off}$ from $$i = i_e \exp(-K_{off} t) \quad (2).$$

The on rate, $K_{off}$ can be determined from $K_{off}$ by fitting the association curve 701 and equation 1 together as is well known in the art for assays such as surface plasmon resonance.

In one embodiment, the present disclosure provides a method of detecting the presence of a protein/antibody in a sensing device as herein described. The method of this embodiment comprises recording a current when a sample suspected of comprising a protein/antibody is in contact with the sensing device as herein described and determining that the protein/antibody is present by detecting an increase in current.

In a second embodiment, the present disclosure provides a method of determining the concentration of a protein/antibody in a sample using a sensing device as herein described. The method of this embodiment comprises recording the time course of current when a sample suspected of comprising a protein/antibody is in contact with the sensing device as herein described and determining the concentration of protein/antibody from the time course of current.

In another embodiment, the method further comprises a calibration step. The calibration step can be performed using (1) a first device comprising two small electrodes, capable of binding only one molecule at a time; followed by (2) a second device comprising two large electrodes, capable of binding a plurality of molecules at a time.

Alternatively, the calibration step can be performed by recording a first time course of current when a first sample comprising a low concentration of protein/antibody is in contact with the sensing device as herein described. After completion of the calibration step, a second time course of current is recorded when a second sample comprising a high concentration of protein/antibody is in contact with the sensing device as herein described.

Figure 8:
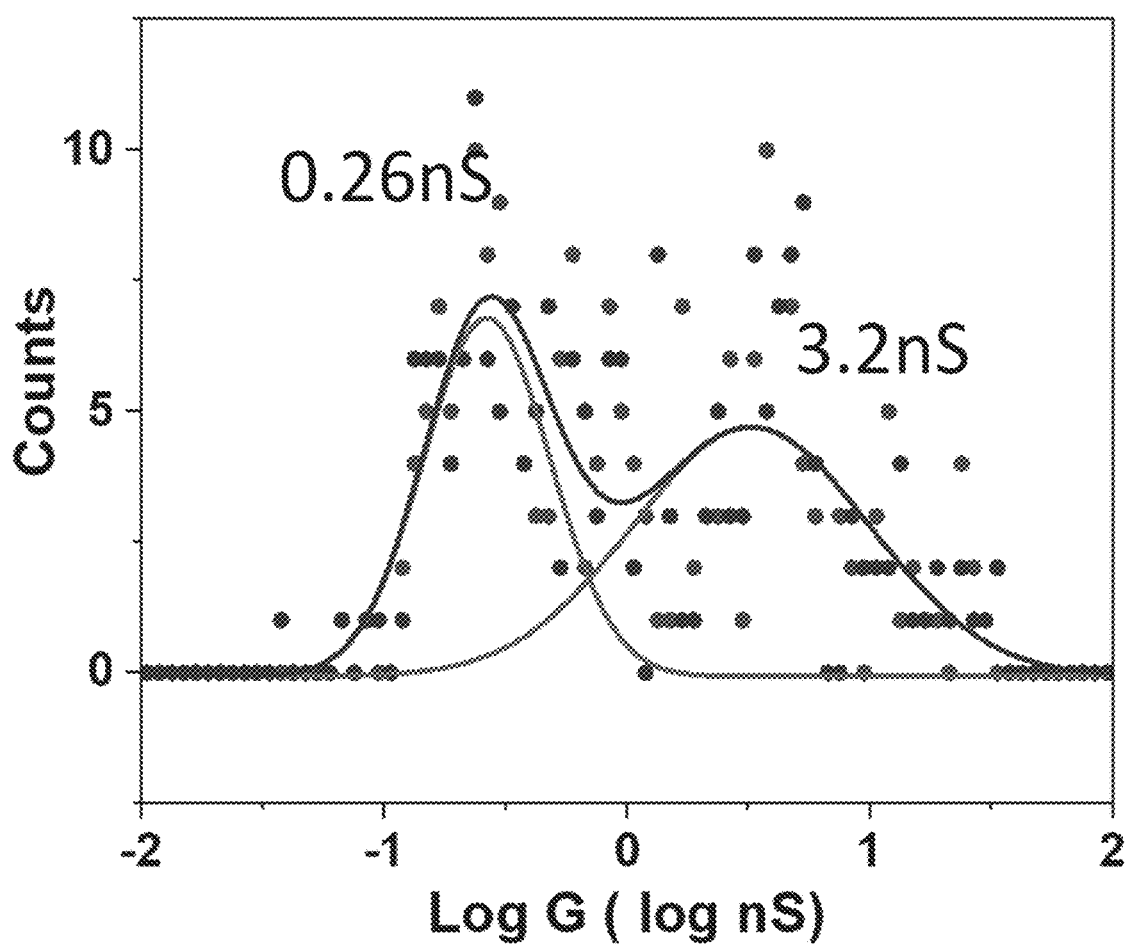
FIG. 8 shows the conductance distribution obtained when a HPVE7 protein on the electrodes binds a single anti-HPV antibody.

FIG. 8 illustrates the two-device calibration step in a method to detect the antibody to the human papillomavirus, HPV. The presence of the antibody to HPV in blood is an indicator for cervical cancer risk. In this embodiment, the device comprises two small electrodes, capable of binding only one molecule at a time. The electrodes were coated with the HPV coat protein HPVE7, which was modified to comprise surface thiols (obtained by treating the protein with SATP (N-succinimidyl-S-acetylthiopropionate) as is well known in the art. The measured single molecule conductance distribution on binding of anti-HPV IgG is shown in FIG. 8. No current was measured in the presence of an isotype, non-binding antibody. The distribution shows the characteristic two peaks generated by antibody binding. (Zhang, B.; Song, W.; Pang, P.; Lai, H.; Chen, Q.; Zhang, P.; Lindsay, S. *Proc Natl Acad Sci USA* 2019.). The smaller conductance (0.26 nS) is a consequence of a single specific binding event at one of the two binding domains of the antibody. The larger conductance peak (3.2 nS) corresponds to specific binding at each of the two binding sites on the antibody. Since the area of the two peaks (approximately height×width) is roughly the same, single binding events are as likely as double binding events. Thus, on average, each binding event contributes 1.73 nS of conductance ((0.26+3.2)/2). Thus, if in a large-area junction comprising a plurality of HPV coat protein HPVE7, 100 nS conductance is measured, then the number of bound molecules is determined to be about 58 (100/1.73).

What is claimed is:

1. A sensing device comprising:
   a first and a second electrode, the first and second electrode being separated by a gap and comprising an opening formed therethrough;
   wherein:
   a plurality of peptide ligands is attached to at least one of the first electrode and the second electrode; wherein each ligand of the plurality of peptide ligands has a length L1 and binds a target protein having a length L2; and the width of the gap is no less than 2L1 and no more than 2L1+L2, such that a detectable signal is produced when the target protein binds a first and a second ligand of the plurality of peptide ligands attached to the first and the second electrodes.

2. The sensing device of claim 1, wherein the first and/or second electrode comprise palladium.

3. The sensing device of claim 1, wherein the plurality of peptide ligands is an epitope specific to the target protein.

4. The sensing device of claim 1, the sensing device further comprising a detector for measuring the detectable signal produced when the target protein binds the first and second ligands attached to the first and second electrodes.

5. The sensing device of claim 1, further comprising a system for introducing and removing buffer and sample.

6. The sensing device of claim 1, further comprising a system for analyzing the detectable signal produced when the target protein binds the first and second ligands attached to the first and second electrodes.

7. A method of detecting the presence of protein in a sensing device, the method comprising:

recording a current when a sample comprising or suspected of comprising a target protein is in contact with the sensing device, wherein the sensing device comprises:

a first and a second electrode, the first and second electrode being separated by a gap and comprising an opening formed therethrough;

wherein:

a plurality of ligands is attached to at least one of the first electrode and the second electrode; wherein each ligand of the plurality of peptide ligands has a length L1 and binds a target protein having a length L2; and the width of the gap is no less than 2L1 and no more than 2L1+L2;

a detector for measuring current produced when the target protein binds a first and a second ligand of the plurality of peptide ligands attached to the first and the second electrodes; and determining that the protein is present by detecting an increase in the current.

8. The method of claim 7, wherein the target protein is an antibody.

9. A method of determining the concentration of a target protein in a sample, the method comprising:

recording a time course of current when a sample comprising or suspected of comprising a protein is in contact with a sensing device, wherein the sensing device comprises:

a first and a second electrode, the first and second electrode being separated by a gap and comprising an opening formed therethrough;

wherein:

a plurality of ligands is attached to at least one of the first electrode and the second electrode; wherein each ligand of the plurality of peptide ligands has a length L1 and binds a target protein having a length L2; and the width of the gap is no less than 2L1 and no more than 2L1+L2;

a detector for measuring the current produced when the target protein binds a first and a second ligand of the plurality of peptide ligands attached to the first and the second electrodes; and determining the concentration of protein from the time course of current.

10. The method of claim 9, wherein the target protein is an antibody.

* * * * *